(12) United States Patent
Watanabe et al.

(10) Patent No.: US 6,214,186 B1
(45) Date of Patent: Apr. 10, 2001

(54) GAS SENSOR HAVING IMPROVED STRUCTURE FOR INSTALLATION OF PROTECTIVE COVER

(75) Inventors: Isao Watanabe, Nagoya; Takashi Kojima, Kasugai; Hirokazu Yamada, Nagoya, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/350,676

(22) Filed: Jul. 12, 1999

(30) Foreign Application Priority Data

| Jul. 13, 1998 | (JP) | 10-197430 |
| Dec. 17, 1998 | (JP) | 10-359194 |
| Dec. 25, 1998 | (JP) | 10-369398 |
| Dec. 25, 1998 | (JP) | 10-369401 |

(51) Int. Cl.[7] .................................................. G01N 27/407
(52) U.S. Cl. ........................................ 204/428; 204/427
(58) Field of Search .................................... 204/421–429

(56) References Cited

U.S. PATENT DOCUMENTS

| 4,756,885 | 7/1988 | Raff et al. | 422/98 |
| 5,762,771 | * 6/1998 | Yamada et al. | 204/427 |
| 5,795,454 | * 8/1998 | Friese et al. | 204/426 |
| 5,830,339 | * 11/1998 | Watanabe et al. | 204/426 |

FOREIGN PATENT DOCUMENTS

| 5-15221 | 3/1993 | (JP) . |
| 5-249069 | 9/1993 | (JP) . |
| 6-32616 | 8/1994 | (JP) . |

* cited by examiner

Primary Examiner—T. Tung
(74) Attorney, Agent, or Firm—Pillsbury Winthrop LLP

(57) ABSTRACT

An improved structure of a gas sensor is provided. The gas sensor includes a gas sensitive element, a holder retaining therein the gas sensitive element, and a protective cover installed on the holder. The protective cover has a flange which is retained in a groove formed in the holder by crimping an outer extension formed on the holder adjacent the groove. The geometries of the groove in the holder and the flange of the protective cover are so determined as to provide for ease of installation of the protective cover on the holder, firm engagement of the protective cover with the groove of the holder, and ease of machining of the groove of the holder.

17 Claims, 18 Drawing Sheets

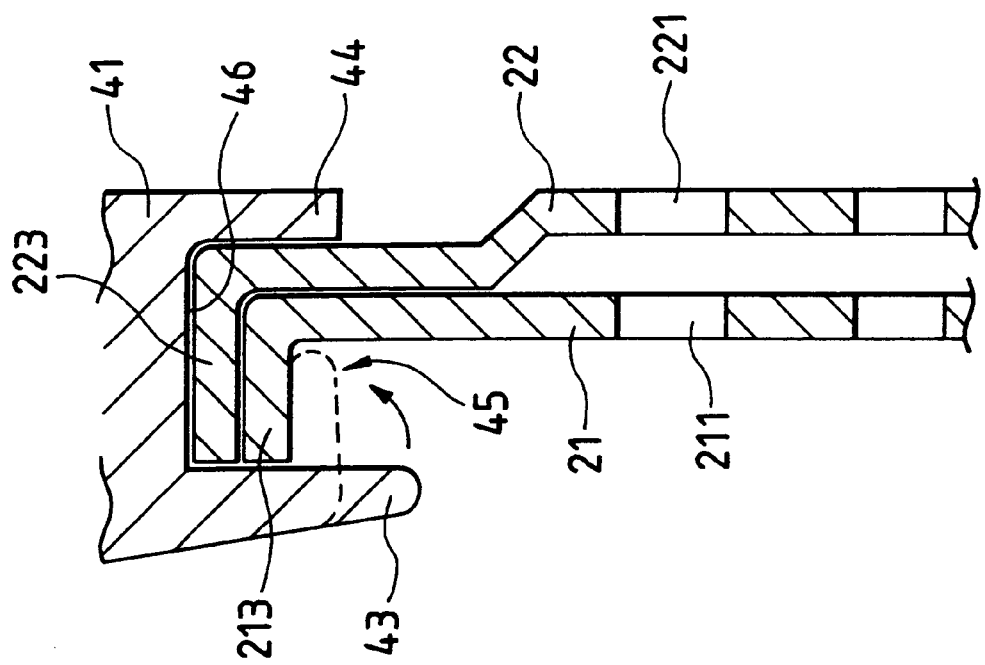
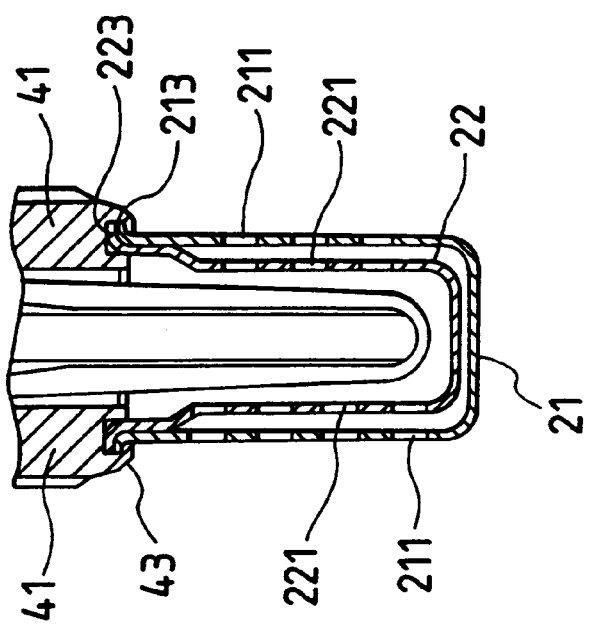

GAS SENSOR HAVING IMPROVED STRUCTURE FOR INSTALLATION OF PROTECTIVE COVER

BACKGROUND OF THE INVENTION

1. Technical Field of the Invention

The present invention relates generally to a gas sensor which may be employed in an air-fuel ratio control system for automotive vehicles for measuring the concentration of gas such $O_2$, NOx, or CO, and more particularly to an improved structure of such a gas sensor which provides for ease of installation of a protective cover on a cover mount, firm engagement of the protective cover with the cover mount, and ease of machining of the cover mount.

2. Background Art

Typical gas sensors employed in measuring the concentration of $O_2$, NOx, or CO in exhaust gasses of an internal combustion engine include a gas sensitive element, a sensor mount, and a protective cover. The sensor mount is used in mounting the sensor in an exhaust pipe and also serves as a holder which retains therein the gas sensitive element. The protective cover is installed on the sensor mount so as to cover the gas sensitive element. The gas sensors usually undergo a temperature change from room temperature to approximately 1000° C. after the engine is started, thereby causing thermal stress to be produced between the sensor mount and the protective cover, which may result in dislodgment of the protective cover from the sensor mount.

SUMMARY OF THE INVENTION

It is therefore a principal object of the present invention to avoid the disadvantages of the prior art.

It is another object of the present invention to provide a simple structure of a gas sensor which provides for ease of installation of a protective cover on a cover mount, firm engagement of the protective cover with the cover mount, and ease of machining of the cover mount.

According to one aspect of the invention, there is provided a gas concentration sensor. The gas concentration sensor comprises: (a) a gas concentration measuring element having a gas-exposed portion exposed to a gas to be measured; (b) a hollow cylindrical holder holding therein the gas concentration measuring element, the holder having an end surface on which an inner and an outer extension are formed to define a groove therebetween, the inner extension being is smaller in height than the outer extension; and (c) a protective cover covering the gas-exposed portion of the gas concentration measuring element, the protective cover having a flange which is retained within the groove of the holder by crimping the outer extension inward to install the protective cover on the end surface of the holder.

In the preferred mode of the invention, a ratio of the height of the inner extension and the height of the outer extension lies within a range of 0.2 to 0.85.

The groove in the end surface of the holder is defined by side walls of the outer and inner extensions, a bottom formed between the side walls of the outer and inner extensions, and a tapered wall extending from the bottom to the side wall of the inner extension.

The height of the inner extension is greater than a thickness of the flange of the protective cover.

The protective cover has a hollow body. The flange of the protective cover consists of a curved portion continuing from the hollow body and a flat portion extending from the curved portion. The flange of the protective cover is retained within the groove of the holder in elastic engagement of an end of the flat portion, the flat portion, and the curved portion with the side wall of the outer extension, the bottom, and the tapered wall, respectively.

At least one inner protective cover is further disposed inside the protective cover. The inner protective cover has a flange retained within the groove of the holder together with the flange of the protective cover by the crimped outer extension.

The inner protective cover may be attached directly to the flange of the protective cover.

The protective cover and the inner protective cover have formed therein gas holes through which the gas enters inside the protective cover and the inner cover. One of the gas holes of the inner protective cover closest to the holder is closer to the holder than one of the gas holes of the protective cover closest to the holder.

The flange of one of the protective cover and the inner protective cover may have a corrugated surface which is in contact with the flange of the other cover.

The holder is formed with a forged member.

The holder is made of material having a hardness lower than that of the protective cover.

According to the second aspect of the invention, there is provided a gas concentration sensor which comprises: (a) a gas concentration measuring element having a gas-exposed portion exposed to a gas to be measured; (b) a hollow cylindrical holder holding therein the gas concentration measuring element, the holder having an end surface on which an inner and an outer extension are formed; (c) a groove formed in the end surface of the holder, the groove being defined by side walls of the outer and inner extensions, a bottom formed between the side walls of the outer and inner extensions, and a tapered wall extending from the bottom to the side wall of the inner extension; and (d) a protective cover covering the gas-exposed portion of the gas concentration measuring element, the protective cover having a flange which is retained within the groove of the holder by crimping the outer extension inward to install the protective cover on the end surface of the holder. In the preferred mode of the invention, the geometry of the groove of the holder is so determined that the flange of the protective cover may be fitted in the groove with a clearance of 0.4 mm or less between the flange and the bottom before the outer extension is crimped.

Specifically, the size and inclination of the tapered wall of the groove may be so determined that the flange of the protective cover may be fitted in the groove with a clearance of 0.4 mm or less between the flange and the bottom before the outer extension is crimped.

According to the third aspect of the invention, there is provided a gas concentration sensor which comprises: (a) a gas concentration measuring element having a gas-exposed portion exposed to a gas to be measured; (b) a hollow cylindrical holder holding therein the gas concentration measuring element, the holder having an end surface on which an inner and an outer extension are formed to define a groove therebetween; (c) an outer protective cover covering the gas-exposed portion of the gas concentration measuring element, the outer protective cover having a flange which is retained within the groove of the holder by crimping the outer extension inward to install the outer protective cover on the end surface of the holder; and (d) an inner protective cover disposed inside the outer protective cover, the inner protective cover having a flange which is retained within the groove of the holder in engagement with the flange of the outer protective cover by crimping the outer extension inward to install the inner protective cover on the end surface of the holder. The flange of one of the outer and inner protective cover has formed thereon protrusions which engage the flange of the other.

In the preferred mode of the invention, a third protective cover is provided which has a flange retained within the groove of the holder in engagement with the flange of one of the outer and inner protective covers which has the protrusions.

The protrusions are formed with undulation of a surface of the flange of the one of the outer and inner protective covers.

The outer protective cover may have the protrusions formed on the flange thereof.

A clearance of 0.05 to 0.2 mm is developed between the inner extension and an inner wall of the inner protective cover.

The holder is made of material having a hardness lower than that of the outer and inner protective covers.

The groove in the end surface of the holder is defined by side walls of the outer and inner extensions, a bottom formed between the side walls of the outer and inner extensions, and a tapered wall extending from the bottom to the side wall of the inner extension. Each of the outer and inner protective covers has a hollow body. The flange of each of the outer and inner protective covers consists of a curved portion continuing from the hollow body and a flat portion extending from the curved portion. The flange of said outer protective cover engages the inner protective cover at a first contact. The curved portion of the flange of the inner protective cover engages the tapered wall of the groove at a second contact. The first contact is located outside the second contact.

The first contact may be made at ends of the flanges of the outer and inner protective covers.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 6(a) is a partially sectional view which shows a top of an oxygen sensor according to the second embodiment of the invention;

FIG. 6(b) is a partially sectional view which shows a pair of protective covers retained in a sensor mount of the oxygen sensor shown in FIG. 6(a);

DESCRIPTION OF THE PREFERRED EMBODIMENTS

Figure 1:
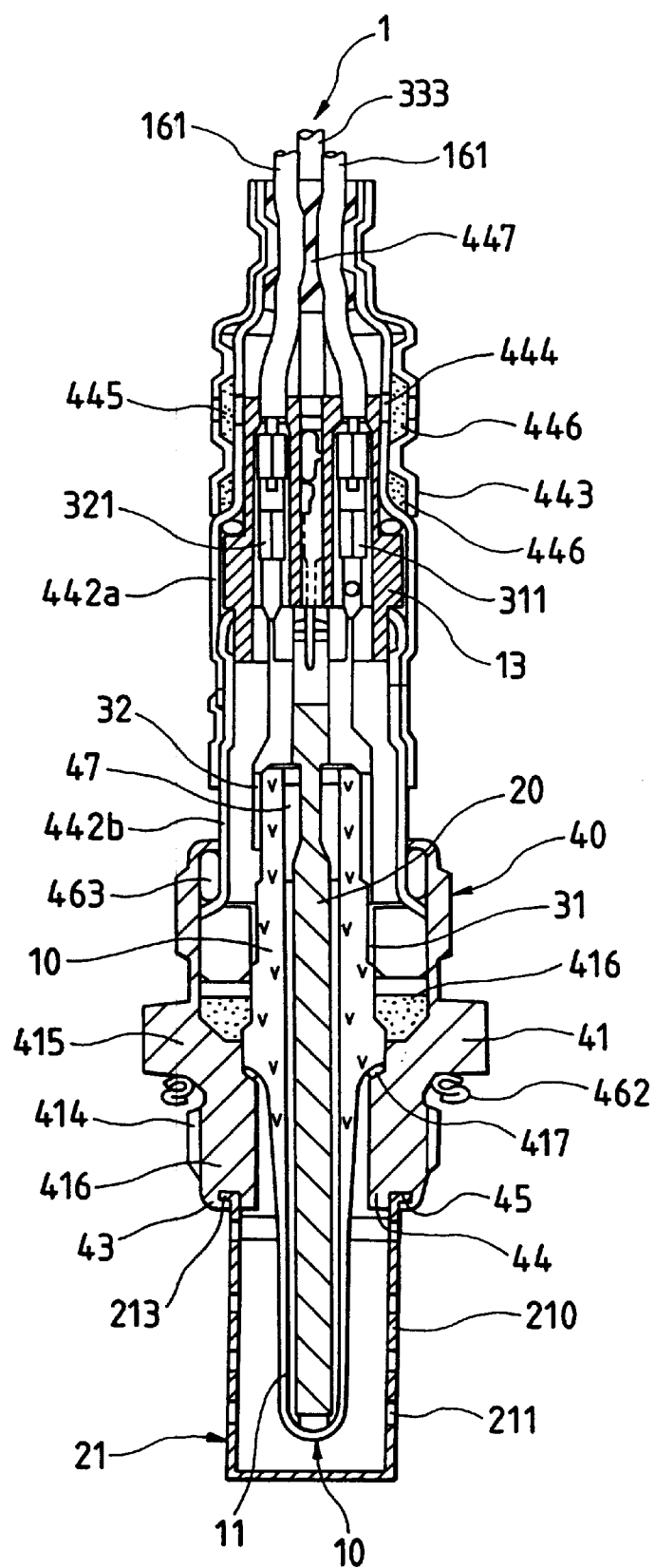
FIG. 1 is a longitudinal cross sectional view which shows an oxygen sensor according to the first embodiment of the invention.

Referring now to the drawings, wherein like numbers refer to like parts in several views, particularly to FIG. 1, there is shown an oxygen sensor 1 according to the first embodiment of the invention which is employed in automotive air-fuel ratio control systems to measure an oxygen content in exhaust gasses of an internal combustion engine. Note that the present invention is not limited to the oxygen sensor and may alternatively be used with any other gas sensors such as HC, CO, and NOx sensors.

The oxygen sensor 1 generally includes an oxygen sensing element 10, a hollow cylindrical housing 40, and a cylindrical protective cover 21. The oxygen sensing element 10 has formed on its end a gas-exposed portion 11 exposed to the gas to be measured. The housing 40 has a sensor mount 41. The sensor mount 41 is, as described later in detail, used for installation of the oxygen sensor 1 and also serves as a holder which holds therein the gas-exposed portion 11 of the oxygen sensing element 10. The protective cover 21 covers the gas-exposed portion 11 of the oxygen sensing element 10 and has formed therein a plurality of gas holes 211 through which the gas flows inside the protective cover 11.

The sensor mount 41 is made of a hollow cylindrical member consisting of a mount flange 415 and a sleeve 416. The sleeve 416 has machined in its end, as clearly shown in FIGS. 2 and 3, an annular groove 45 of a given depth to form an outer annular extension 43 and an inner annular extension 44. Within the groove 45, a flange 213 of the protective cover 21 is fitted in contact of an upper flat surface with the bottom 46 of the groove 45 and retained by crimping or bending the outer extension 43 inward.

Figure 2:
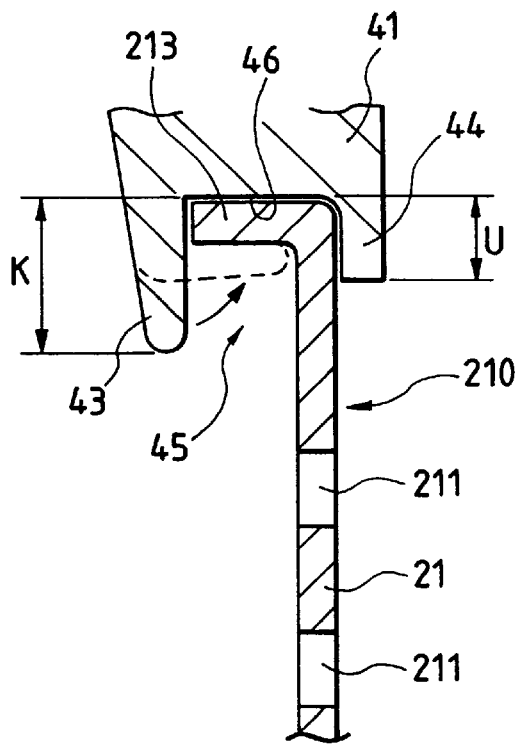
FIG. 2 is a partially sectional view which shows a sensor mount and a protective cover.
Figure 3:
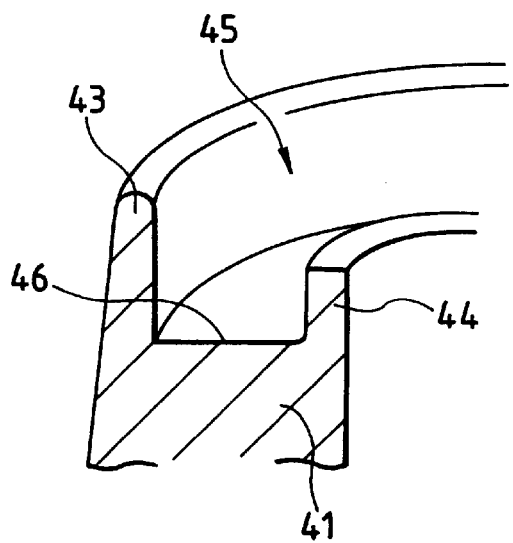
FIG. 3 is a partially perspective view which shows a groove formed in a sensor mount.

The height U of the inner extension 44 of the sensor mount 41, as shown in FIG. 2, is smaller than the height K of the outer extension 43. The height K of the outer extension 43 is greater than the thickness of the flange 213 of the protective cover 21. In this embodiment, the height U of the inner extension 44 is 1.4 mm. The height K of the outer extension 43 is 2.4 mm. It is advisable that the heights U and K be determined so that the ratio U/K may lie within a range of 0.2 to 0.85, preferably 0.35 to 0.75 for machinability of the groove 45 and the protective cover 21 and ability to retain the protective cover 21 within the groove 45.

Figure 5:
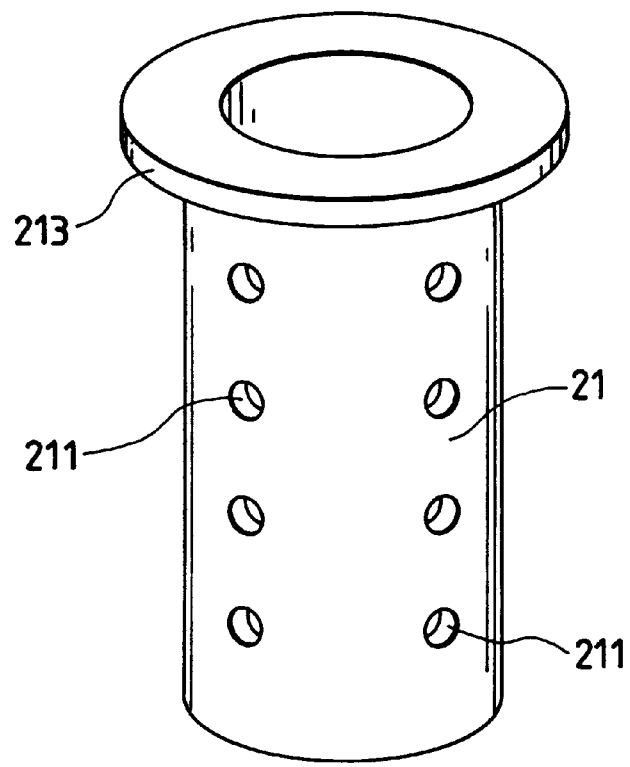
FIG. 5 is a perspective view which shows a protective cover.

The protective cover 21, as clearly shown in FIG. 5, has a hollow cylinder 210 and the flange 213 formed on an open end of the cylinder 210. The cylinder 210 has formed therein the gas holes 211 through which the gas to be measured flows.

The sensor mount 41 is made of stainless steel SUS430 having a hardness Hv of approximately 220. The protective cover 21 is made of stainless steel SUS310CP having a hardness Hv of approximately 350. The sensor mount 41 is, thus, softer than the protective cover 21 so that the flange 213 of the protective cover 21 can bite into the annular groove 45 of the sensor mount 41 by crimping the outer extension 43 firmly, thus allowing the protective cover 21 to be retained on the sensor mount 41 without any play in a circumferential direction. Further, the crimping of the outer extension 43 causes the sensor mount 41 (i.e., the groove 45) to be pressed elastically, which will produce reactive force to increase an elastic nip of the flange 213 in a lengthwise direction of the protective cover 21.

The inner extension 44 of the sensor mount 41 has a minimum height (i.e., the height q enough to support an inner wall of the end of the protective cover 21 which is, as described above, smaller than that of the outer extension 43 used in retaining the protective cover 21, thereby minimizing the length of a cylindrical space defined between an inner wall of the cylinder of the sensor mount 41 and an outer wall of the oxygen sensing element 10. This suppresses reaction of carbon sticking to the oxygen sensing element 10 with platinum of electrodes provided in the oxygen sensing element 10 and prevents the carbon from growing, thus avoiding the deterioration of the electrodes caused by a deposit of the carbon and peeling of a coating from the oxygen sensing element 10, which assures an increased service life of the oxygen sensor.

Figure 4:
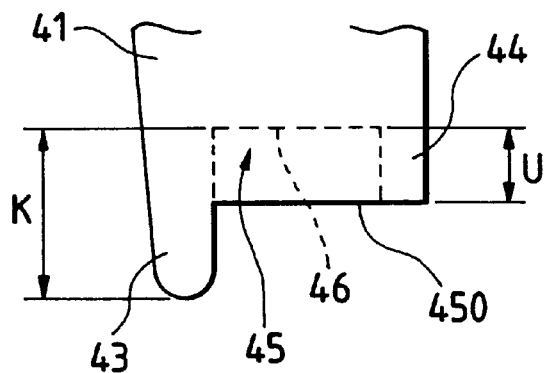
FIG. 4 is an illustration which shows a relation of height between outer and inner extensions on a sensor mount.

The formation of the annular groove 45 is, as shown in FIG. 4, accomplished by first preparing a forged housing block having a stepped or shoulder portion 450 formed on an end thereof and machining the shoulder portion 450 to a depth corresponding to the height U of the inner extension 44. This results in a decrease in machining load by an amount corresponding to the difference in height between the outer and inner extensions 43 and 44 (i.e., K–U) as compared with a conventional structure wherein outer and inner extensions have the same height. The decrease in machining load is also promoted by integral formation of the outer extension 43 on the housing block.

The decreased height U of the inner extension 44 also facilitates ease of fitting of the flange 213 of the protective cover 21 into the annular groove 45, thus resulting in ease of installation of the protective cover 21 on the sensor mount 41.

The oxygen sensor 1 of this embodiment is, as described above, designed as an air-fuel ratio sensor measuring the air-fuel ratio in an internal combustion engine for automotive vehicles.

The installation of the oxygen sensor 1 in the vehicle is accomplished by screwing threads 414 formed on the outer wall of the sensor mount 41 to a threaded hole in an exhaust pipe of the engine. The mount flange 415 is in contact with the outer wall of the exhaust pipe through a gasket 462.

The oxygen sensor 1 also includes outer and inner covers 442a and 442b, an end cover 443, and a water-repellent filter 446. The inner cover 442b is joined at an end to an upper end of the housing 40 through a metallic ring 463. The outer cover 442a is joined to an upper portion of the inner cover 442b by crimping. The end cover 443 covers the upper end of the outer cover 442a. The end cover 443 and the outer cover 442a have air vents 445 and 444 formed in alignment which communicate with each other through the water-repellent filter 446 for introducing through an air passage (not shown) the reference gas, e.g., the air into a chamber within which the oxygen sensing element 10 is disposed.

The oxygen sensing element 10 is retained in the sensor mount 41 through packing 417 and talc 416 and includes an oxygen ion conductive solid electrolyte body and a measuring and a reference electrode disposed on outer and inner surfaces of the electrolyte body.

A bar-shaped heater unit 20 is retained within the oxygen sensing element 10 through a holder 47. The heater unit 20 includes a heating conductor which connects with a feeder 333 and which heats the measuring and reference electrodes of the oxygen sensing element 10 up to a temperature at which the oxygen concentration is able to be measured correctly.

Leads 161 and the feeder 333 are retained within the covers 442a and 443 through a rubber bush 447. The leads 161 connect with the electrodes of the oxygen sensing element 10 through connectors 311 and 321 and signal pickup lines 31 and 32, respectively. The connectors 311 and 321 are disposed within an insulating glass block 13 mounted in the covers 442a and 442b.

For a more detailed structure and operation of the oxygen sensor 1, reference is made to U.S. application Ser. No. 09/196,693, filed on Nov. 20, 1998, assigned to the same assignee as that of this application, disclosure of which is incorporated herein by reference.

FIGS. 6(a) and 6(b) show the second embodiment of the invention.

An inner cover 22 is, as clearly shown in FIG. 6(b), disposed inside the protective cover 21. The inner cover 22 has, similar to the protective cover 21, a mount flange 223 which is secured in the annular groove 45 by crimping the outer extension 43 of the sensor mount 41 together with the mount flange 213 of the protective cover 21 and a plurality of gas holes 221 formed in a side wall thereof which communicate with the gas holes 211 of the protective cover 21. The inner cover 22 serves as a protector which protects the oxygen sensing element 10 from impact along with the protective cover 21. Other arrangements are identical with those of the first embodiment, and explanation thereof in detail will be omitted here.

Figure 7:
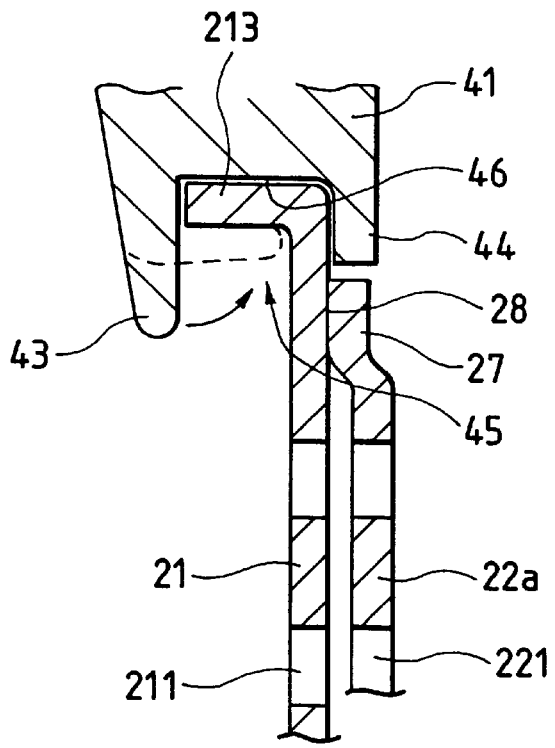
FIG. 7 is a partially sectional view which shows a pair of protective covers retained in a sensor mount according to the third embodiment of the invention.

FIG. 7 shows the third embodiment of the invention which has an inner cover 22a serving as a protector, like the inner cover 22 of the second embodiment. The inner cover 22a has a bulged end portion 27 which is attached to an inner wall of the protective cover 21 at a welded portion 28. The location of the welded portion 28 is not limited to the illustrated one and may be on a corner of the bottom of the inner cover 22a. The mount flange 213 of the protective cover 21 is, similar to the first embodiment, retained by the outer extension 43 of the sensor mount 41. Other arrangements are identical with those of the first embodiment, and explanation thereof in detail will be omitted here.

Figure 8:
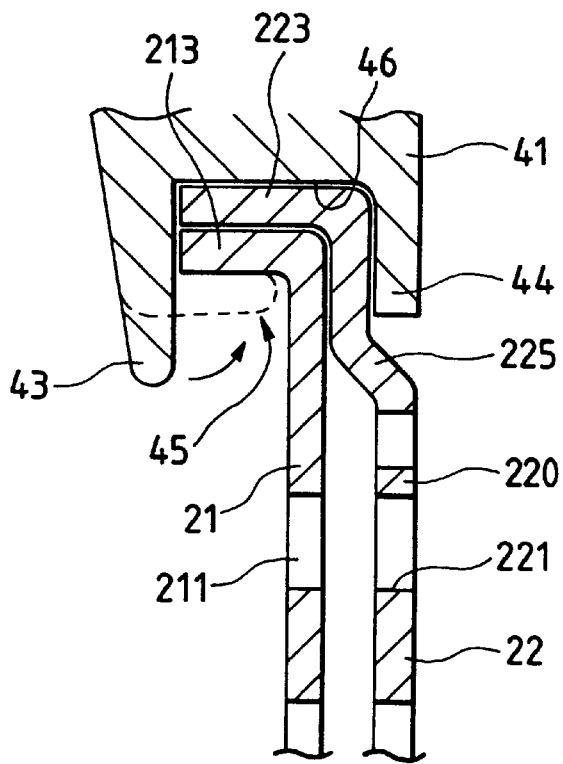
FIG. 8 is a partially sectional view which shows a pair of protective covers retained in a sensor mount according to the fourth embodiment of the invention.

FIG. 8 shows the fourth embodiment of the invention which is a modification of the second embodiment in FIGS. 6(a) and 6(b).

The inner cover 22 has a funnel-shaped portion 225 connecting the mount flange 223 and the cylindrical body 220 of the inner cover 22. The funnel-shaped portion 225 is closer to the inner extension 44 of the sensor mount 41 than the second embodiment, thereby increasing an outer area of the cylindrical body 220, thus resulting in an increase in freedom in designing the gas holes 221.

Figure 9:
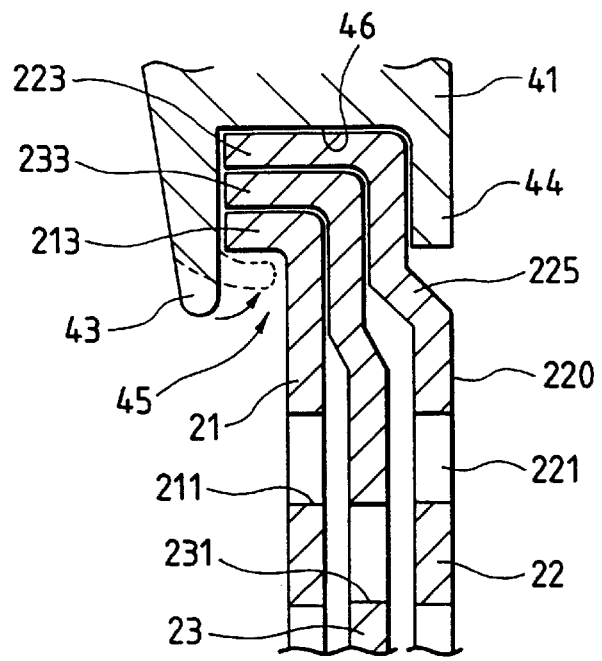
FIG. 9 is a partially sectional view which shows three protective covers retained in a sensor mount according to the third embodiment of the invention.

FIG. 9 shows the fifth embodiment of the invention which is a modification of the fourth embodiment and which has an intermediate protective cover 23 disposed between the protective cover 21 and the inner cover 22. The intermediate protective cover 23 has a mount flange 233 which is retained within the groove 45 of the sensor mount 41 together with the mount flanges 213 and 223 of the protective cover 21 and the inner cover 22. The intermediate protective cover 23 has gas holes 231 formed in a cylindrical body thereof which establish fluid communication between the gas holes 211 and 221. Other arrangements are identical with those of the fourth embodiment, and explanation thereof in detail will be omitted here.

Figure 10:
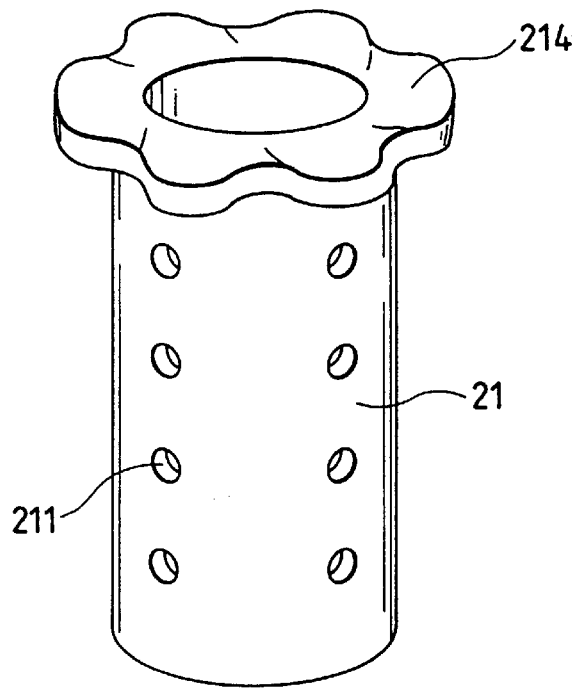
FIG. 10 is a perspective view which shows a protective cover according to the sixth embodiment of the invention.

FIG. 10 shows the sixth embodiment of the invention.

The protective cover 21 of this embodiment has the mount flange 214 with a corrugated periphery. The mount flange 213 is also waved in a thickness-wise direction thereof so that it may be elastically deformed when pressed against the bottom 46 of the groove 45 by crimping the outer extension 43 of the sensor mount 41, thereby increasing an elastic nip of the flange 214 between the bottom of the groove 45 and the outer extension 43 in lengthwise and circumferential directions of the protective cover 21. Other arrangements are identical with those of the first embodiment, and explanation thereof in detail will be omitted here. The mount flange 223 of the inner cover 22 may also be corrugated like the mount flange 214 of the protective cover 21.

Figure 11:
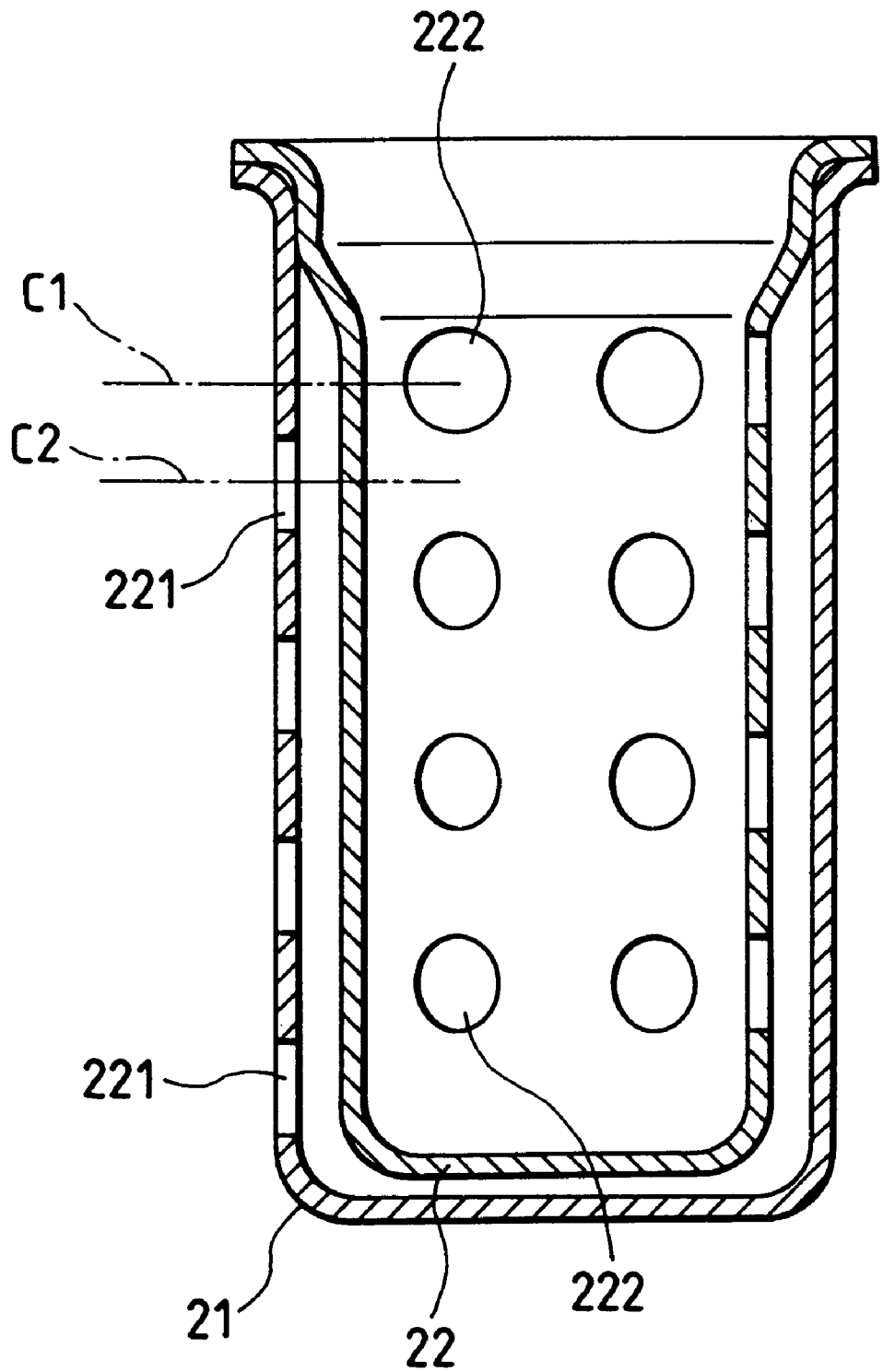
FIG. 11 is a cross sectional view which shows a pair of protective covers according to the seventh embodiment of the invention.

FIG. 11 shows the seventh embodiment of the invention which has, similar to the second embodiment, the inner cover 22.

The protective cover 21 and the inner cover 22 have gas holes 221 and 222, respectively. The gas holes 221 are arranged at regular intervals. Similarly, the gas holes 222 are arranged at regular intervals. One of horizontal arrays of the gas holes 222 of the inner cover 22 closest to the sensor mount 41 lies on a line C1 which is shifted at a given interval away from a line C2 on which one of horizontal arrays of the gas holes 221 of the protective cover 21 closest to the sensor mount 41 lies so that the gas holes 222 may be out of alignment with the gas holes 221, thereby causing the gas to flow from the gas holes 221 to the gas holes 222, and vice versa, through the whole of a chamber defined between the protective cover 21 and the inner cover 22, thus enhancing an exchange of gasses to be measured.

Figure 12A:
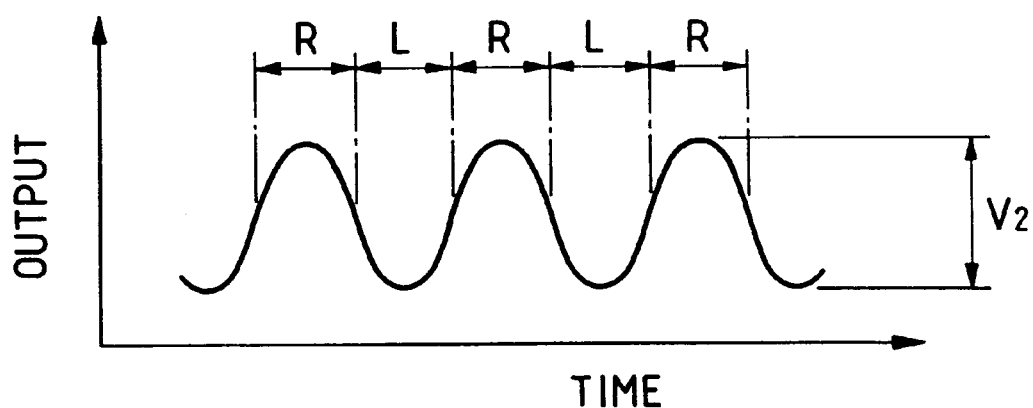
FIG. 12(a) is a graph which shows a variation in output of an oxygen sensor.
Figure 12B:
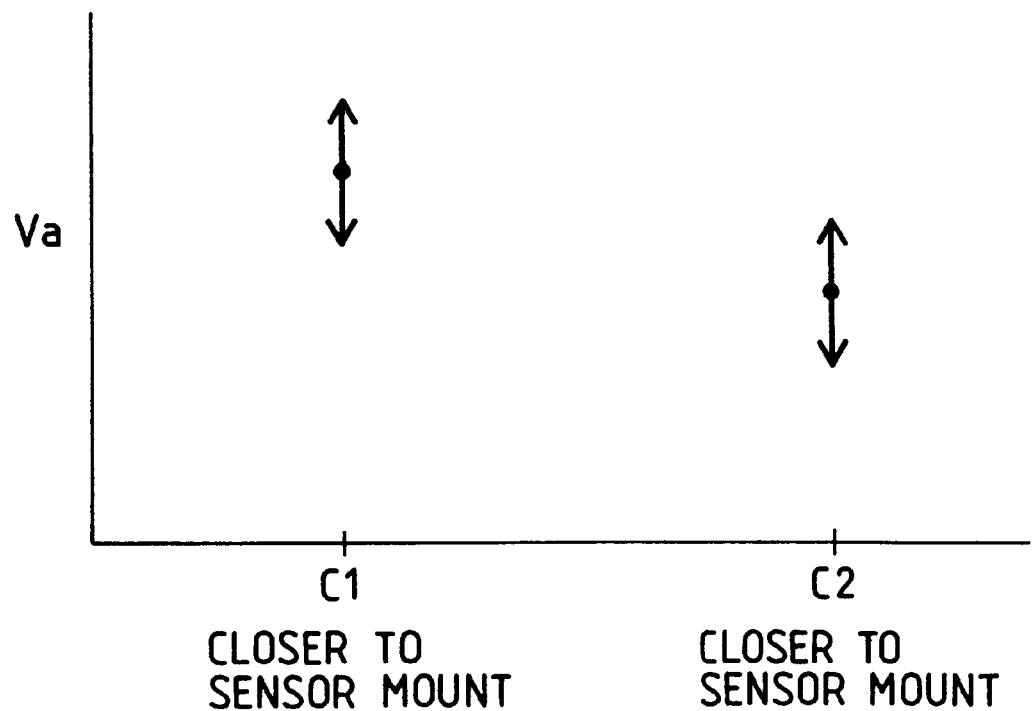
FIG. 12(b) is a graph which shows amplitudes of outputs of an oxygen sensor in which line C1, as shown in FIG. 11, is closer to a sensor mount than line C2 and an oxygen sensor in which line C2 is closer to the sensor mount than line C1.
Figure 13:
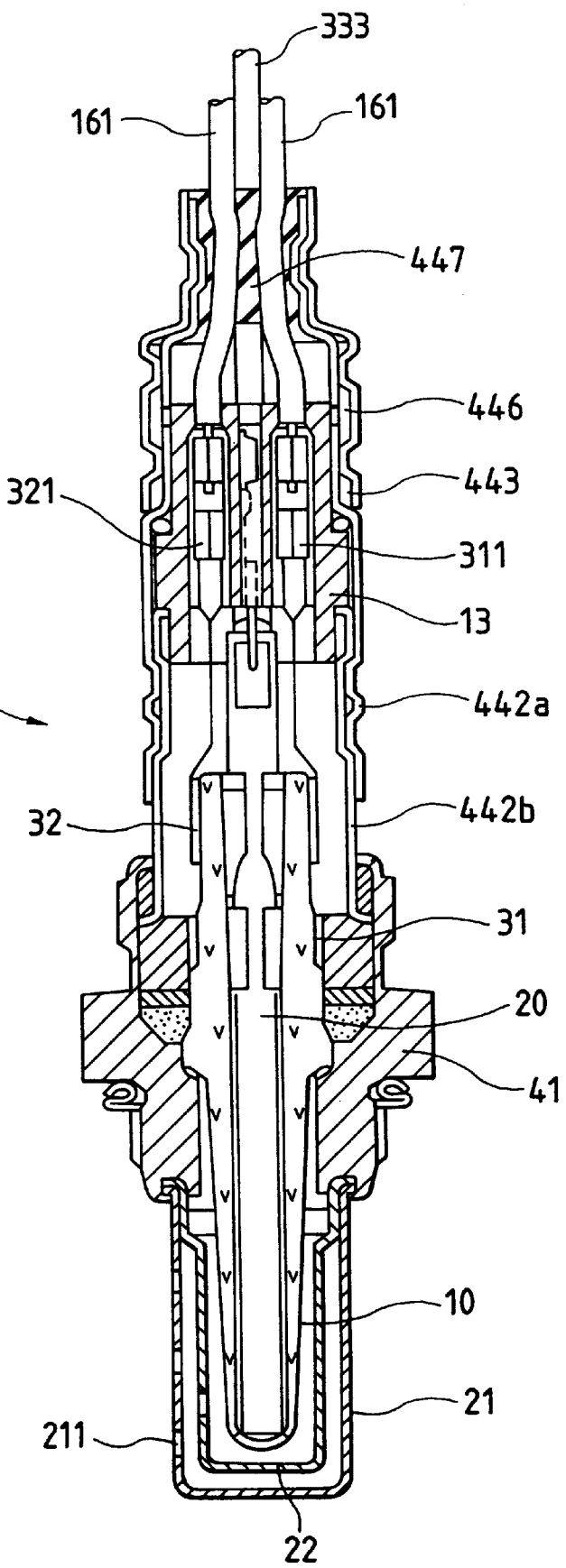
FIG. 13 is a longitudinal cross sectional view which shows an oxygen sensor according to the eighth embodiment of the invention.

The oxygen sensor 1 installed in the exhaust pipe of the engine outputs a signal, as shown in FIG. 12(a), which changes in level cyclically with a change in air-fuel ratio of a mixture. Portions of the signal, as labeled "R" indicate rich air-fuel ratios, while portions, as labeled "L" indicate lean air-fuel ratios. The inventors of this application prepared two oxygen sensors one of which has the line C1 of the inner cover 22, as shown in FIG. 11, located closer to the sensor mount 41 than the line C2 and the other of which has the line C2 of the protective cover 21 located closer to the sensor mount 41 than the line C1 and measured amplitudes Va of outputs of the two oxygen sensors. The results are shown in FIG. 12(b). It is found that the oxygen sensor in which the line C1 of the inner cover 22 is located closer to the sensor mount 41 than the line C2 has a greater amplitude Va, thus increasing the efficiency of an exchange of exhaust gasses to be measured.

FIGS. 13 to 17 show the oxygen sensor 1 according to the eighth embodiment of the invention.

Figure 15:
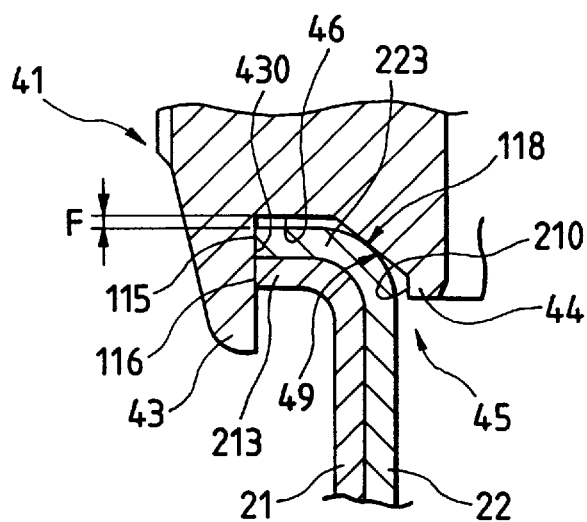
FIG. 15 is a partially sectional view which shows a pair of protective covers fitted within a groove before an outer extension on a sensor mount is crimped.

The protective cover 21 and the inner cover 22 are installed at the mount flanges 213 and 223 in the annular groove 45 of the sensor mount 41. The mount flanges 213 and 223 are, as shown in FIG. 15, bent outward. The mount flange 223 has a radius of curvature of 1.1 mm at an inside corner 118.

Figure 17:
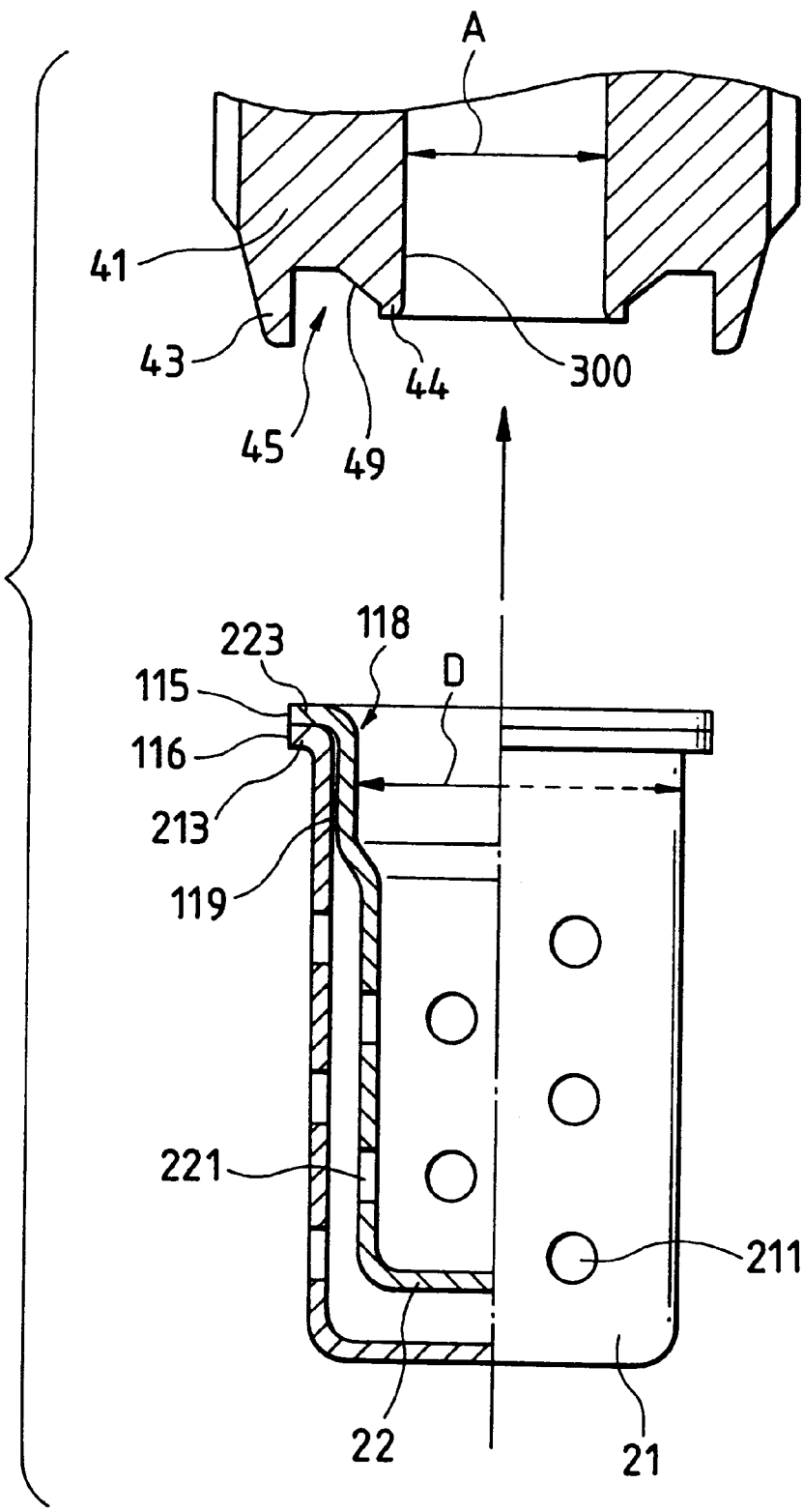
FIG. 17 is an illustration which shows the protective covers, as illustrated in FIG. 15, before installed on the sensor mount.

The sensor mount 41, as shown in FIG. 17, has a cylindrical chamber having a diameter A of 8.2 mm. The inner cover 22 has a bulged end portion of a diameter D of 9.9 mm.

Figure 14:
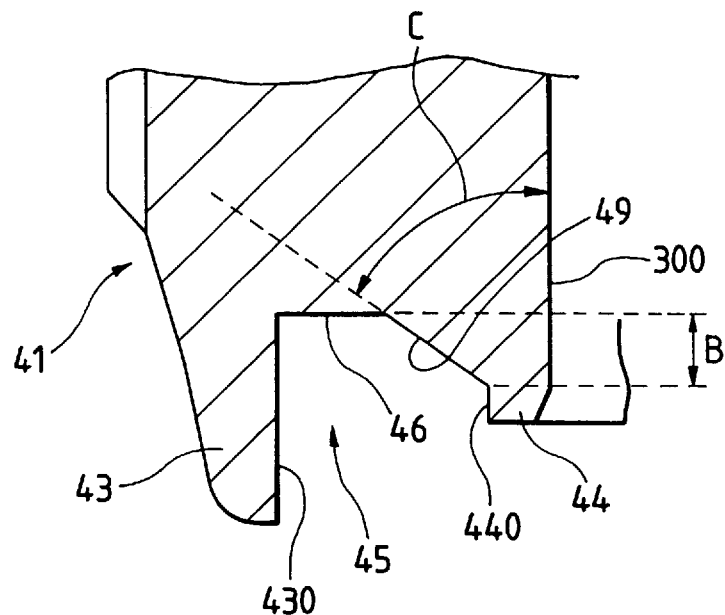
FIG. 14 is a partially sectional view which shows an annular groove formed in a sensor mount of the eighth embodiment.

The annular groove 45 is, as clearly shown in FIG. 14, defined by an inner side wall 440 of the inner extension 44, an inner side wall 430 of the outer extension 43, an annular flat bottom 46, and a slope or tapered wall 49. The tapered wall 49 connects the bottom 46 and the inner side wall 440 and is oriented at an angle C of 45° relative to the inner cylindrical wall 300 of the sensor mount 41. The height B of the tapered wall 49 is 0.9 mm. The inclination (i.e., the angle C) and height B of the tapered wall 49 may be determined within ranges that create, as shown in FIG. 15, a clearance F of 0.4 mm or less, preferably 0.05 to 0.3 mm between the mount flange 223 of the inner cover 22 and the bottom 46.

The sensor mount 41, as shown in FIG. 17, has a cylindrical chamber having a diameter A of 8.2 mm and is made of SUS430. The protective cover 21 and the inner cover 22 are made of SUS310S.

The installation of the protective cover 21 and the inner cover 22 on the sensor mount 41 is accomplished in the following manner. First, the protective cover 21 and the inner cover 22 are welded together, as indicated at 119 in FIG. 17, just below the mount flanges 213 and 223. Next, the mount flanges 213 and 223 are, as clearly shown in FIG. 15, fitted in the groove 45 with engagement between of the corner 118 of the inner cover 22 and ends 115 and 116 of the mount flanges 223 and 213 with the tapered wall 49 and the inner side wall 430, respectively. The clearance F between the mount flange 223 of the inner cover 22 and the bottom 46 is 0.15 mm. The ends 115 and 116 of the mount flanges 223 and 231 may alternatively be separate from the inner side wall 430.

Figure 16:
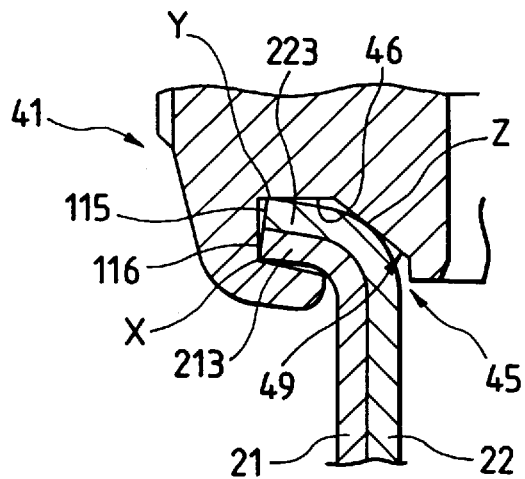
FIG. 16 is a partially sectional view which shows the protective covers in the groove, as illustrated in FIG. 15, after the outer extension on the sensor mount is crimped.

Finally, the outer extension 43 is bent inward, as shown in FIG. 16, to press the mount flanges 213 and 223 against the bottom 46 and the tapered wall 49, thereby causing the mount flanges 223 and 213 to be deformed elastically, that is, lifted upward, as viewed in the drawing, thus resulting in firm engagement of the mount flanges 213 and 223 with the groove 45 at three points X, Y, and Z in cross section (i.e., outer edges of the mount flanges 213 and 223 and the corner 118).

The protective cover 21 and the inner cover 22 may alternatively be installed in the sensor mount 41 by crimping without being welded at numeral 119 in FIG. 17.

The protective cover 21 and the inner cover 22 are, as described above, made of the stainless steel different from that of the sensor mount 41, so that a difference in coefficient of thermal expansion therebetween will be approximately $7 \times 10^{-6}$ at 800° C. The oxygen sensor 1 is, as described above, installed in the exhaust pipe of the engine and thus undergoes a temperature change from room temperature to approximately 1000° C. after the engine is started. This will cause thermal stress to be produced between the sensor mount 41 and the covers 21 and 22, which leads to elastic deformation of the mount flanges 213 and 223 across the corners thereof, thus further increasing tight engagement of the mount flanges 213 and 223 with the groove 45.

Figure 18:
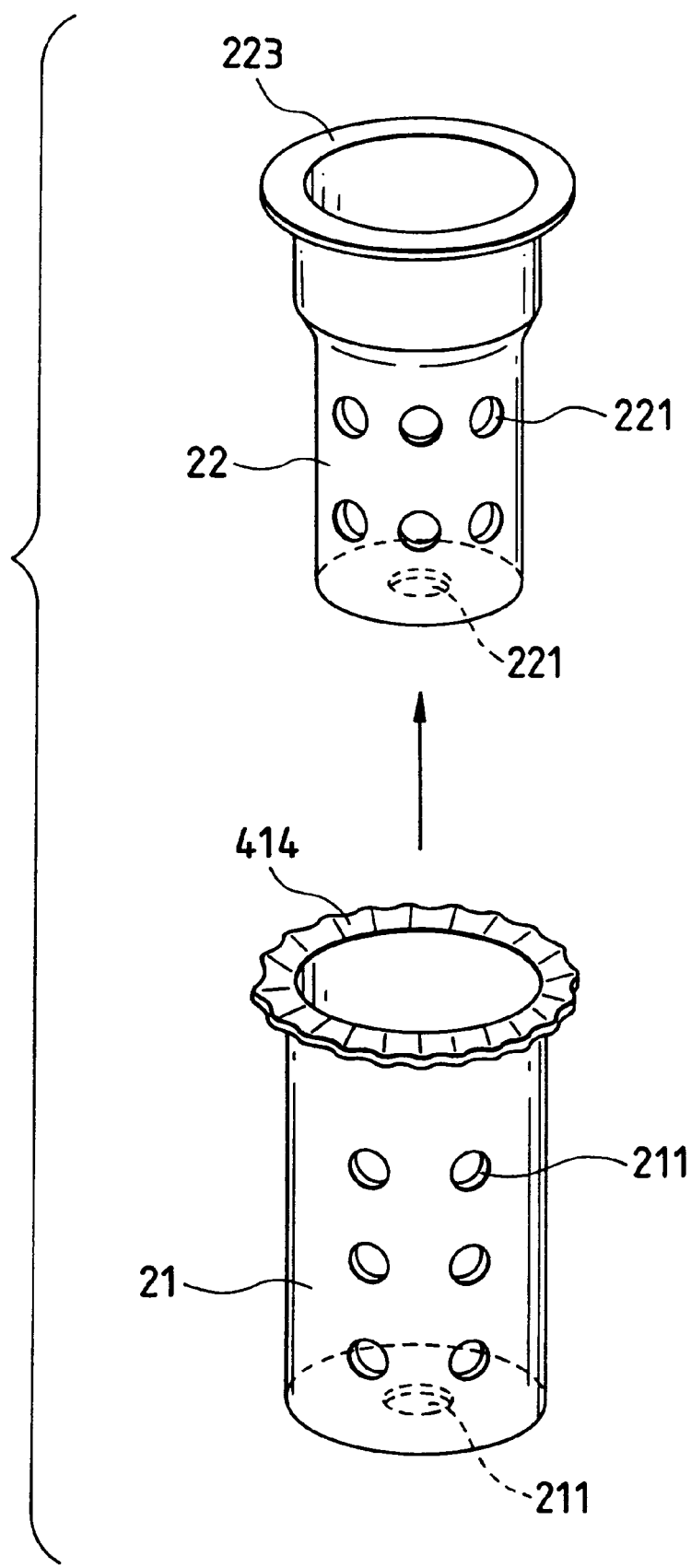
FIG. 18 is a perspective view which shows a pair of protective covers according to the ninth embodiment of the invention.
Figure 19:
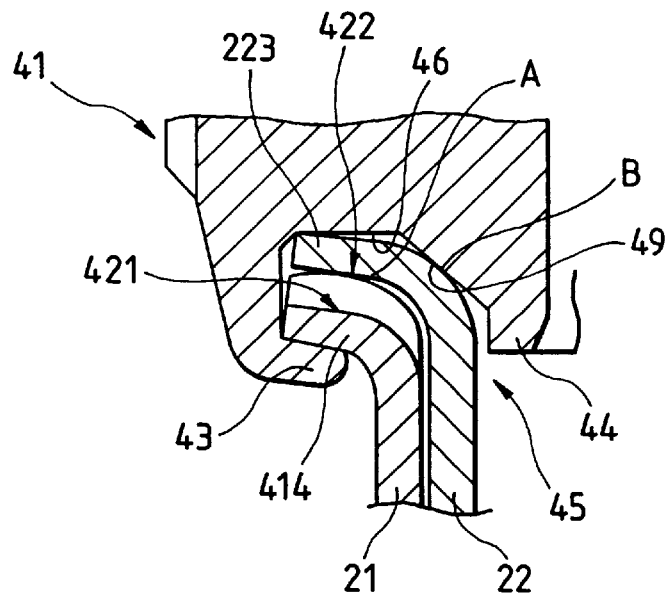
FIG. 19 is a partially sectional view which shows installation of flanges of the protective covers, as illustrated in FIG. 18, within a groove of a sensor mount.

FIGS. 18 and 19 show the ninth embodiment of the invention which is different from the eighth embodiment only in structure of the protective cover 21. Other arrangements are identical, and explanation thereof in detail will be omitted here.

The protective cover 21 has a mount flange 414 corrugated in a width-wise direction. Specifically, the mount flange 414 is waved to form, as shown in FIG. 19, protrusions 422 (i.e., tops of waves) and recesses 421 (i.e., troughs of the waves). Thus, when the mount flanges 414 of the protective cover 21 and the mount flange 223 of the inner cover 22 are pressed by bending the outer extension 43 of the sensor mount 41 inward, it will cause the mount flange 414 to be deformed elastically so that the protrusions 422 and the recesses 421 move close to each other, that is, the mount flange 414 is flattened, which will produce elastic force urging the inner cover 223 and the outer extension 43 of the sensor mount 41 in opposite directions, thus resulting in an increased nip of the mount flanges 223 and 414 between the bottom 46 and the tapered wall 49 of the groove 45 and the outer extension 43.

It is advisable that the mount flanges 223 and 414 be arranged in the groove 45 so that a contact point A of the mount flanges 223 and 414, as shown in FIG. 19, may be located outside a contact point B of the mount flange 223 and the tapered wall 49. This positional relation causes the pressure produced by crimping the outer extension 43 of the sensor mount 41 exerted on the protective cover 21 and the inner cover 22 to be transformed into rotation moment or torque oriented around the contact B clockwise, as viewed in the drawing, thereby allowing a nip of ends of the mount flanges 223 and 414 between the bottom 46 of the groove 45 and the outer extension 43 to be increased.

The contact A of the mount flanges 223 and 414 is preferably made at the ends thereof, thereby maximizing the torque around the contact B.

The positional relation between the contacts A and B may also be achieved in the eighth embodiment shown in FIG. 16.

Figure 20A:
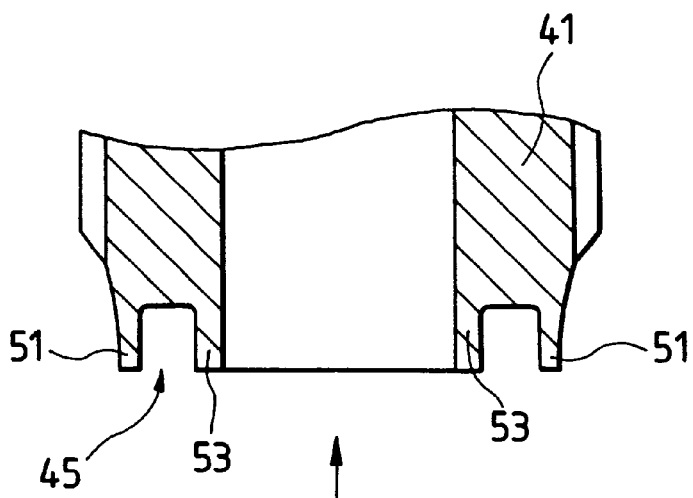
FIG. 20(a) is a partially sectional view which shows a sensor mount according to the tenth embodiment of the invention.
Figure 20B:
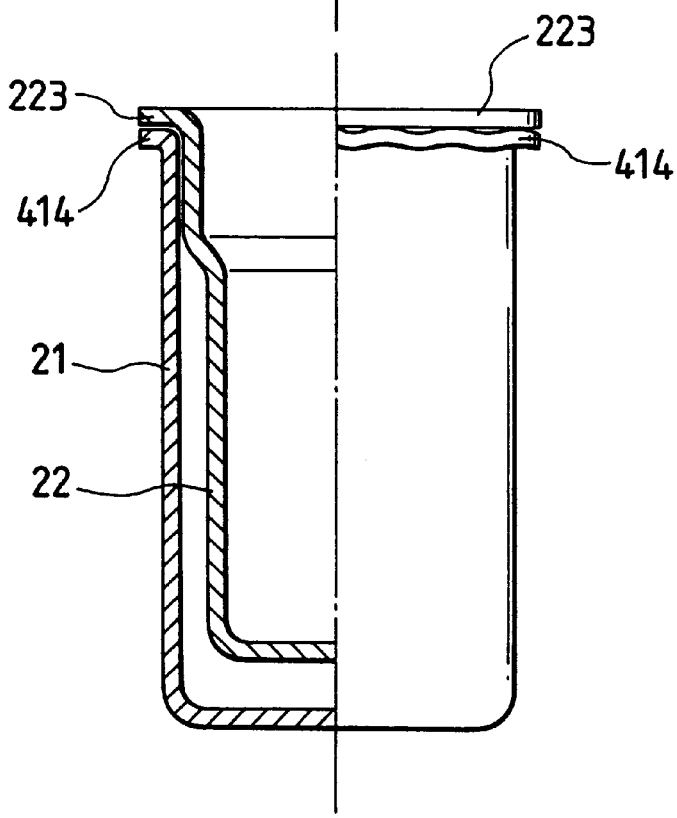
FIG. 20(b) is a partially sectional view which shows a pair of protective covers according to the tenth embodiment of the invention.
Figure 21:
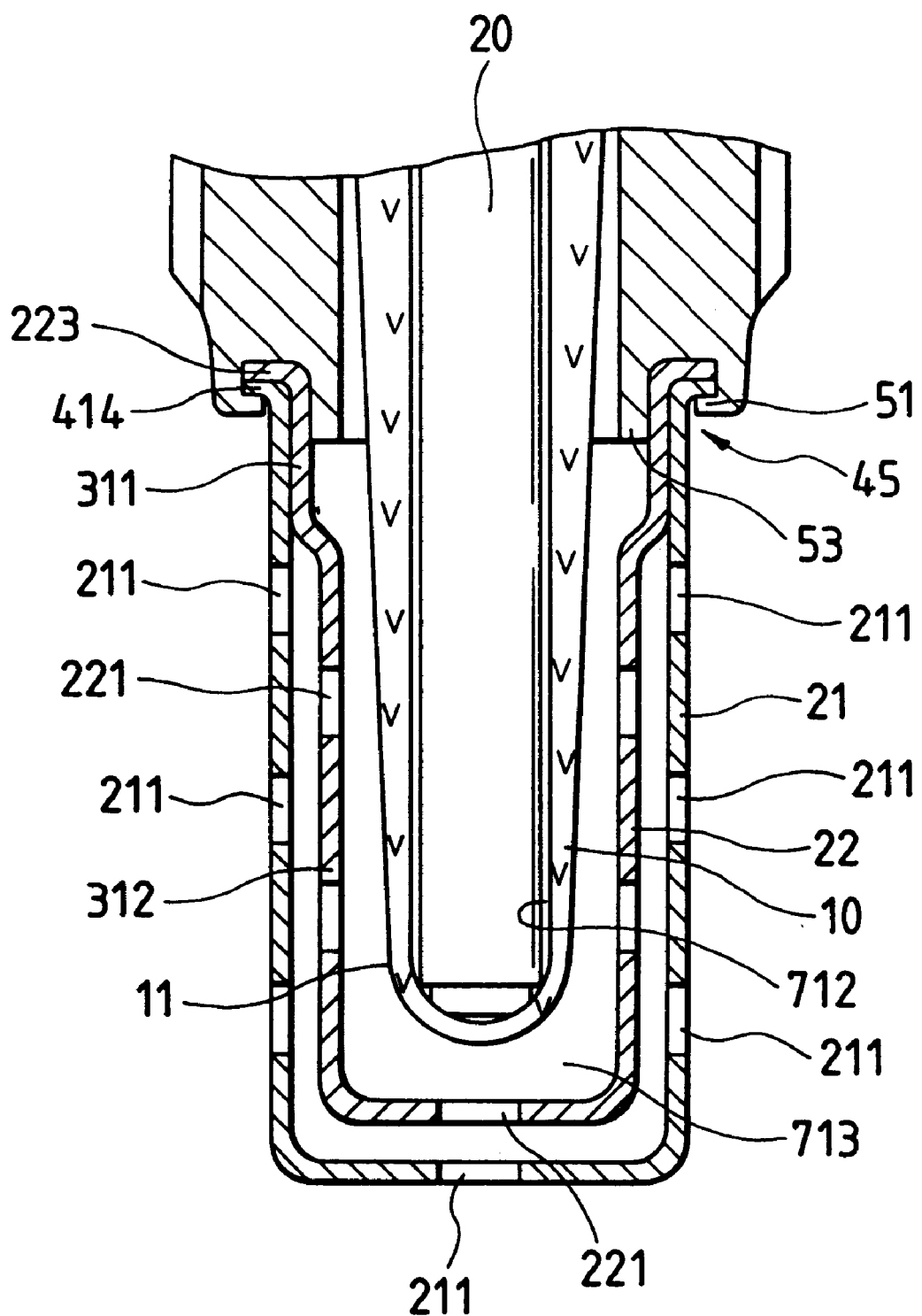
FIG. 21 is a partially sectional view which shows the protective covers, as illustrated in FIG. 20(b), installed on a sensor mount.

FIGS. 20(a), 20(b), and 21 show the tenth embodiment of the invention which is a modification of the ninth embodiment in FIGS. 18 and 19.

The sensor mount 41, as clearly shown in FIG. 20(a), has formed in its end an annular groove 45 to form outer and inner annular extensions 51 and 53 having substantially the same height.

The protective cover 21 and the inner cover 22 are identical in structure with the ones shown in FIG. 18. Specifically, the inner cover 22, as clearly shown in FIG. 21, consists of a bulged portion 311 and a sleeve portion 312 with a bottom and has two horizontal arrays of eight gas holes 221 formed in the sleeve portion 312 and one gas hole 221 formed in the bottom (the total number of the gas holes 221 is seventeen). The bulged portion 311 has formed at an end thereof the mount flange 223 which has a flat surface contact with the bottom of the groove 45. The protective cover 21 has three horizontal arrays of eight gas holes 211 formed in a side wall and one gas hole 211 formed in a bottom (the total number of the gas holes 211 is twenty four). The protective cover 21 also has the corrugated flange 414 identical with the one shown in FIG. 18. Instead of the protective cover 21, the inner cover 22 may have the corrugated flange 414.

The installation of the protective cover 21 and the inner cover 22 on the sensor mount 41 is, as shown in FIG. 21, achieved by crimping the outer extension 51 of the sensor mount 41 at a bend angle of approximately 90° to retain the mount flanges 223 and 414 within the groove 45. The crimping of the outer extension 51 causes the corrugated mount flange 414 of the protective cover 21 to be deformed in a thickness-wise direction thereof, thereby producing elastic pressure urging the mount flange 223 of the inner cover 22 and the outer extension 51 of the sensor mount 41 in opposite directions, thus resulting in an increased nip of the mount flanges 223 and 414 between the bottom of the groove 45 and the outer extension 51.

Reference numerals 712 and 713 in FIG. 21 indicate a reference and a measuring chamber, respectively. The reference chamber 712 leads to the atmosphere through the air vents 444 and 445 as shown in FIG. 1. The measuring chamber 713 is filled with the gas to be measured.

Figure 22:
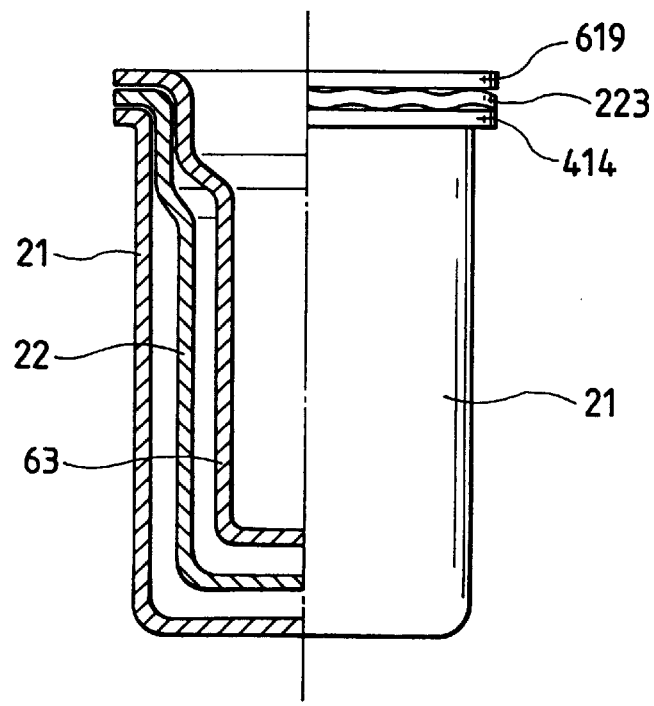
FIG. 22 is a partially sectional view which shows three protective covers installed on a sensor mount according the eleventh embodiment of the invention.

FIG. 22 shows the eleventh embodiment of the invention which is different from the tenth embodiment in FIGS. 20(a), 20(b), and 21 in that a second inner cover 63 having a flat mount flange 619 is disposed inside the inner cover 22 and in that the mount flange 223 of the inner cover 22 is corrugated in a thickness-wise direction, while the mount flange 414 of the protective cover 21 is flattened. Other arrangements are identical, and explanation thereof in detail will be omitted here.

FIGS. 23(a) to 23(f) show examples of corrugation of the mount flange 414 of the protective cover 21 in the tenth embodiment or the mount flange 223 of the inner cover 22 in the eleventh embodiment.

Figure 23A:
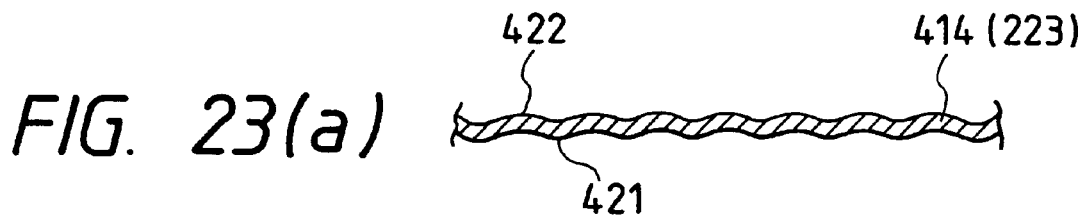
FIGS. 23(a), 23(b), 23(c), 23(d), 23(e), and 23(f) are partially sectional views which show a variety of examples of corrugation of a flange of a protective cover.

The waves of the mount flange 414 or 223 in FIG. 23(a) have the same radius of curvature at the tops 322 and the troughs 421.

Figure 23B:
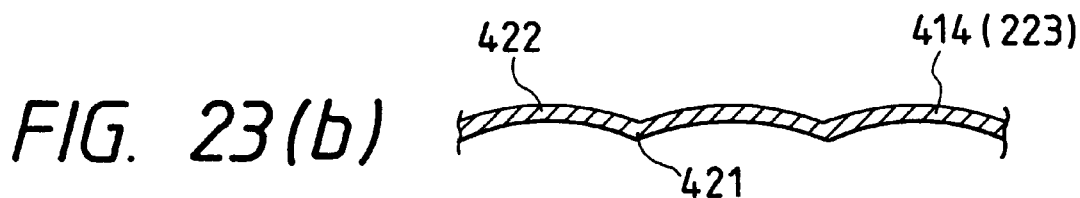

The waves of the mount flange 414 or 223 in FIG. 23(b) have different radii of curvature at the tops 322 and the troughs 421.

Figure 23C:
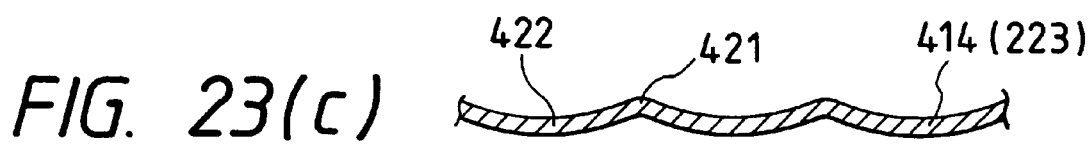

The waves of the mount flange 414 or 223 in FIG. 23(c) are mirror images of the ones in FIG. 23(b).

Figure 23D:
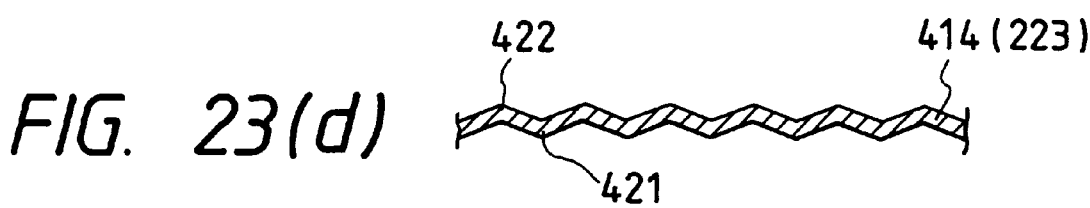

The mount flange 414 or 223 in FIG. 23(d) is waved like bellows.

Figure 23E:
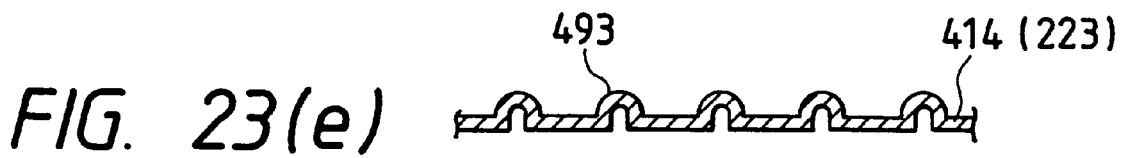

The mount flange 414 or 223 in FIG. 23(e) has waves 493 of U-shape in cross section formed thereon at regular intervals.

Figure 23F:
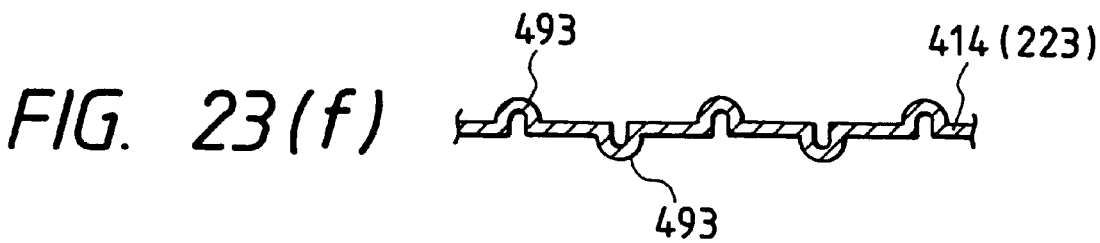

The mount flange 414 or 223 in FIG. 23(f) has waves 493 of U-shape in cross section formed on an upper and a lower surface thereof alternately.

The inventors of this application performed endurance tests applying 90G six samples E1 to E4, C1, and C2 of the oxygen sensor 1 using an impact tester.

Figure 25:
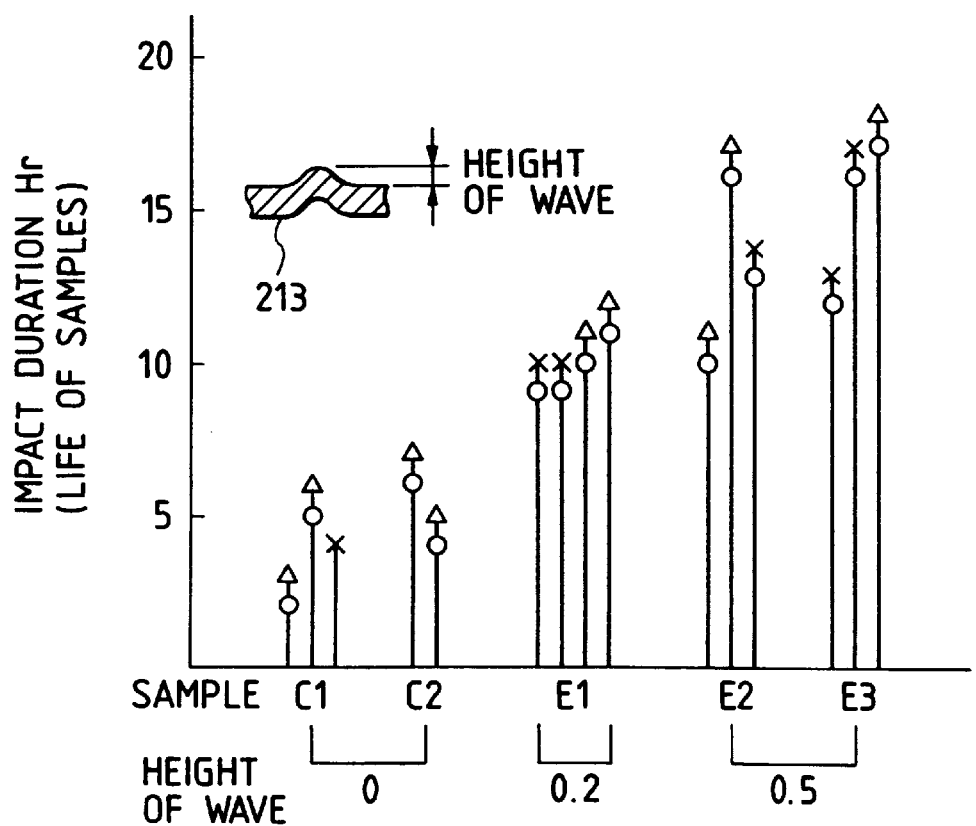
FIG. 25 is a graph which shows results of endurance tests performed for different heights of waves formed on a flange of a protective cover.

The sample E1 has an assembly of the protective cover 21 in which the mount flange 414 has a thickness of 0.5 mm and waves formed thereon whose height (distance, as shown in FIG. 25, between the top and the trough of the wave minus the thickness of the mount flange 414) is 0.2 mm and the inner cover 22 in which the mount flange 223 has a thickness of 0.5 mm.

The sample E2 is identical with the sample E1 except that the height of the waves formed on the mount flange 414 is 0.5 mm.

The sample E3 is identical with the sample E2 except that the mount flanges 414 and 223 have a thickness of 0.6 mm.

Figure 24:
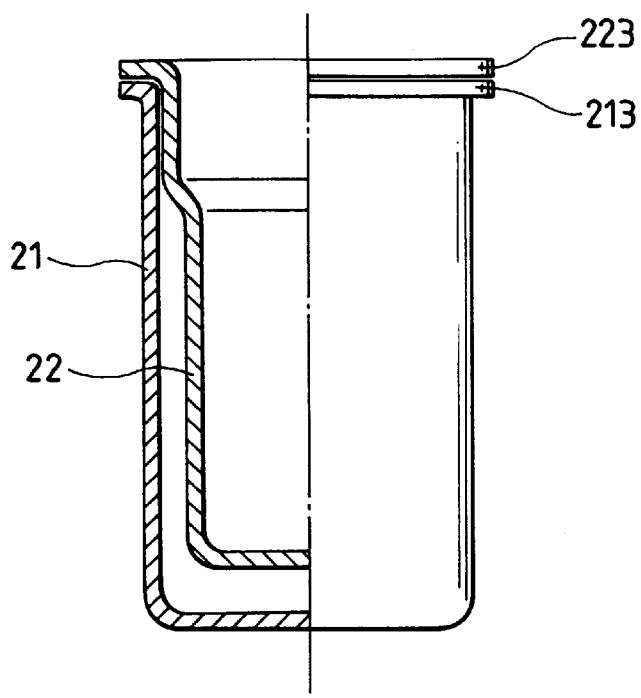
FIG. 24 is a partially sectional view which shows a comparative sample of a combination of an inner cover and a protective cover with a flat mount flange for endurance tests.

The sample C1 is identical with the sample E1 except that the protective cover 21 has, as shown in FIG. 24, the flat mount flange 213.

The sample C2 is identical with the sample C1 except that the mount flanges 213 and 223 have a thickness of 0.6 mm.

The results of the tests are illustrated in a graph of FIG. 25. "○" indicates the length of time each sample withstood the impact without any looseness of the assembly of the protective cover 21 and the inner cover 22 within the groove 45 of the sensor mount 41. "Δ" indicates the time when unwanted play occurred between the assembly of the covers 21 and 22 and the groove 45. "×" indicates the time when the assembly of the covers 21 and 22 was dislodged from the groove 45. Each sample were tested two to four times. The graph shows that the samples E1 to E2 in which the mount flange 414 of the protective cover 21 are undulated all have the durability higher than that of the samples C1 and C2 and the durability increases as the thickness of each of the mount flanges 223, 424, and 213 increases. The graph also shows that the sample E1 in which the height of the waves of the mount flange 414 is 0.2 mm has a variation in durability. It is, thus, found that the oxygen sensor 1 has the stable durability when the height of the waves of the mount flange 414 of the protective cover 22 is more than 0.2 mm.

The inventor of this application also tested six samples of the oxygen sensor 1 in the tenth embodiment for durability for different clearances between an outer side wall of the inner extension 53 of the sensor mount 41 and an inner wall of the inner cover 22. Note that the clearance between the outer side wall of the inner extension 53 and the inner wall of the inner cover 22 is defined by one-half of a difference between inner diameter of the inner cover 22 and outer diameter of the inner extension 53.

Figure 26:
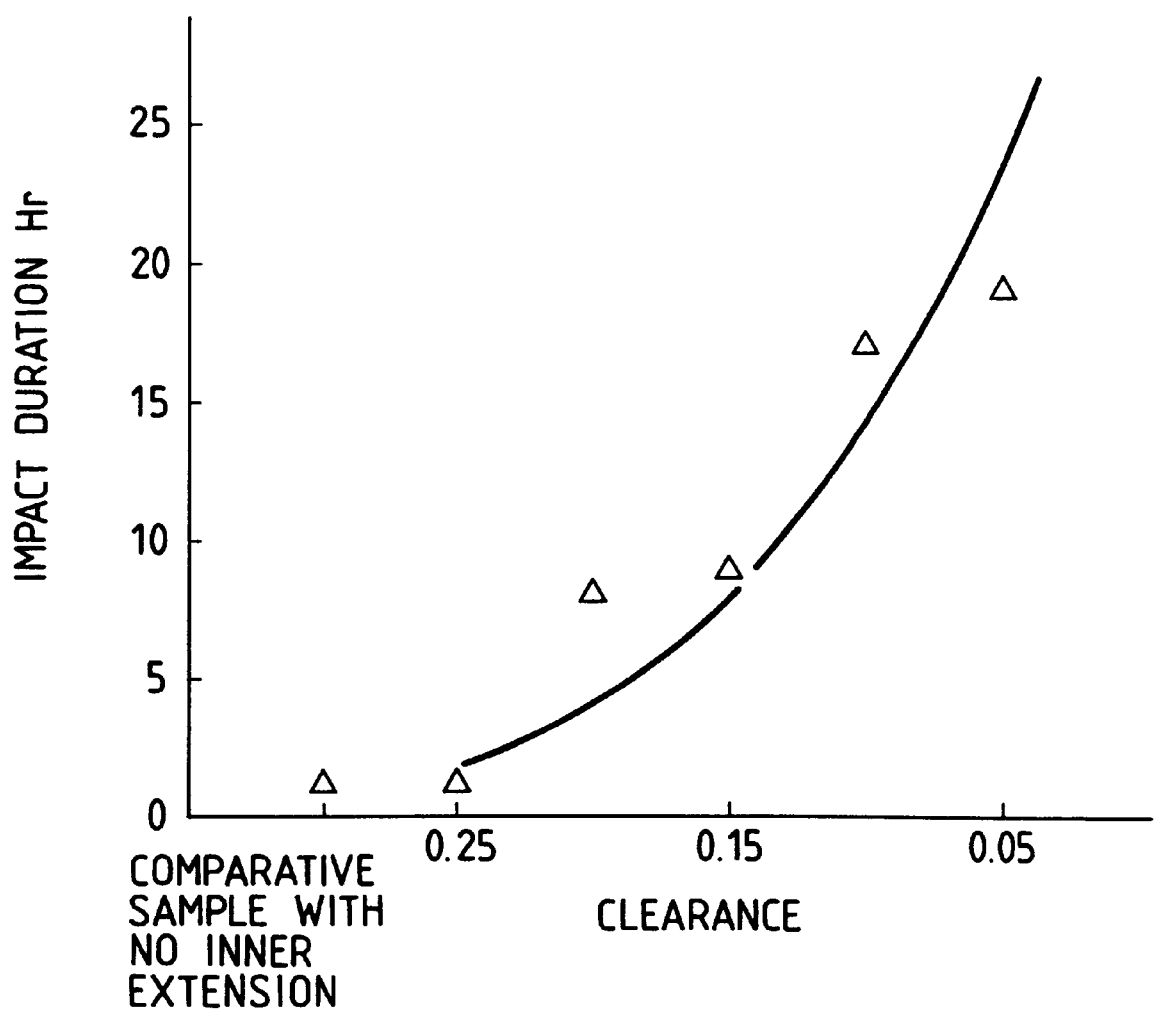
FIG. 26 is a graph which shows results of endurance tests performed for different clearances between an outer side wall of an inner extension on a sensor mount and an inner wall of an inner cover.

Five of the six samples have different clearances of 0.05 to 0.25 mm. The other is a comparative sample in which the sensor mount 1 does not have the inner extension 53. 90G heating impact tests were performed by applying an impact force of 90G to the samples 800 to 1000 times per minute at ambient temperatures of 800 to 900° C. The results of the tests are shown in a graph of FIG. 26. "Δ" indicates the time when unwanted play occurred between the assembly of the covers 21 and 22 and the groove 45.

The graph shows that the sample in which the clearance between the outer side wall of the inner extension 53 of the sensor mount 41 and the inner wall of the inner cover 22 is 0.25 mm has substantially the same durability of that of the comparative sample and that the durability increases as the clearance decreases. Usually, it is difficult to decrease the clearance below 0.05 mm for installation of the assembly of the covers 21 and 22 within the groove 45. It is, thus, advisable that the clearance between the outer side wall of the inner extension 53 of the sensor mount 41 and the inner wall of the inner cover 22 be in a range of 0.05 to 0.20 mm.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

The oxygen sensor 1 of each embodiment may include the oxygen sensing element 10 formed with laminations. For example, U.S. Pat. No. 5,573,650, issued Nov. 12, 1996 to Fukaya et al., teaches such a structure of the oxygen sensing element 10, disclosure of which is incorporated herein by reference.

The gas holes 221, 221, and 222 may alternatively be formed with slits.

While the sensor mount 41 is made of the stainless steel SUS430 having a hardness Hv of approximately 220, and the protective cover 21 is made of the stainless steel SUS310CP having a hardness Hv of approximately 350, the mount flanges 223 and 619 of the inner covers 22 and 63 may also be made of stainless steel harder than the sensor mount 41 for increasing bite of the flanges 223 and 619 into the groove 45 of the sensor mount 41.

What is claimed is:

1. A gas concentration sensor comprising:

a gas concentration measuring element having a gas-exposed portion to be exposed to a gas to be measured;

a hollow cylindrical holder holding therein said gas concentration measuring element, said holder having an end surface on which an inner and an outer extension are formed;

a groove formed in the end surface of said holder, said groove being defined by side walls of the outer and inner extensions, a bottom formed between the side walls of the outer and inner extensions, and a tapered wall extending from the bottom to the side wall of the inner extension; and a protective cover covering the gas-exposed portion of said gas concentration measuring element, said protective cover having a flange which is retained within the groove of said holder by crimping the outer extension inward to install said protective cover on the end surface of said holder, said flange making elastic engagement at at least three portions thereof with the side wall of the outer extension, the bottom, and the tapered wall of the groove.

2. A gas concentration sensor as set forth in claim 1, wherein said protective cover has a hollow body, the flange of said protective cover consisting of a curved portion continuing from the hollow body and a flat portion extending from the curved portion, and wherein the flange of said protective cover is retained within the groove of said holder in elastic engagement of an end of the flat portion, the flat portion, and the curved portion with the side wall of the outer extension, the bottom, and the tapered wall, respectively.

3. A gas concentration sensor as set forth in claim 1, wherein the geometry of said groove of said holder is so determined that the flange of said protective cover may be fitted in the groove with a clearance of 0.4 mm or less between the flange and the bottom before crimping the outer extension.

4. A gas concentration sensor as set forth in claim 1, wherein the size and inclination of the tapered wall of said groove are so determined that the flange of said protective cover may be fitted in the groove with a clearance of 0.4 mm or less between the flange and the bottom before crimping the outer extension.

5. A gas concentration sensor as set forth in claim 1, wherein the flange of said protective cover is retained firmly within the groove under elastic pressures which are produced by elastic point engagement of said three portions of the flange with the side wall of the outer extension, the bottom, and the tapered wall of the groove and oriented in different directions.

6. A gas concentration sensor as set forth in claim 5, wherein said three portions of the flange comprise two end portions of the flange, opposed in a thickness-wise direction of the flange, and a curved, base portion of the flange.

7. A gas concentration sensor as set forth in claim 1, wherein said three portions of the flange comprise two end portions of the flange, opposed in a thickness-wise direction of the flange, and a curved, base portion of the flange.

8. A gas concentration sensor comprising:
a gas concentration measuring element having a gas-exposed portion to be exposed to a gas to be measured;
a hollow cylindrical holder holding therein said gas concentration measuring element, said holder having an end surface on which an inner and an outer extension are formed to define a groove therebetween;
an outer protective cover covering the gas-exposed portion of said gas concentration measuring element, said outer protective cover having a flange which is retained within the groove of said holder by crimping the outer extension inward to install said outer protective cover on the end surface of said holder; and
an inner protective cover disposed inside said outer protective cover, said inner protective cover having a flange which is retained within the groove of said holder in engagement with the flange of said outer protective cover by crimping the outer extension inward to install said inner protective cover on the end surface of said holder,
wherein the flange of one of said outer and inner protective covers has formed thereon protrusions and the flange of the other of said outer and inner protective covers does not have protrusions, said protrusions engaging the flange of the other of said outer and inner protective covers.

9. A gas concentration sensor as set forth in claim 8, further comprising a third protective cover having a flange retained within the groove of said holder in engagement with the flange of one of said outer and inner protective covers which has the protrusions.

10. A gas concentration sensor as set forth in claim 8, wherein the protrusions are formed with undulation of a surface of the flange of the one of said outer and inner protective covers.

11. A gas concentration sensor as set forth in claim 8, wherein said outer protective cover has the protrusions formed on the flange thereof.

12. A gas concentration sensor as set forth in claim 8, wherein the inner extension of said holder has an inner annular wall facing an inner wall of said inner protective cover.

13. A gas concentration sensor as set forth in claim 8, wherein a clearance of 0.05 to 0.2 mm is developed between the inner extension and an inner wall of said inner protective cover.

14. A gas concentration sensor as set forth in claim 8, wherein said holder is made of material having a hardness lower than that of said outer and inner protective covers.

15. A gas concentration sensor as set forth in claim 8, wherein the groove in the end surface of said holder is defined by side walls of the outer and inner extensions, a bottom formed between the side walls of the outer and inner extensions, and a tapered wall extending from the bottom to the side wall of the inner extension, and wherein each of said outer and inner protective covers has a hollow body, the flange of each of said outer and inner protective covers consisting of a curved portion continuing from the hollow body and a flat portion extending from the curved portion, the flange of said outer protective cover engaging said inner protective cover at a first contact, the curved portion of the flange of said inner protective cover engaging the tapered wall of the groove at a second contact, the first contact being located outside the second contact.

16. A gas concentration sensor as set forth in claim 15, wherein the first contact is made at ends of the flanges of the outer and inner protective covers.

17. A gas concentration sensor as set forth in claim 8, wherein the flanges of said outer and inner protective covers are arranged so as to overlap each other to establish firm engagement of the protrusions formed on said one of the flanges with a surface of said other flange.

* * * * *